(12) United States Patent
Apffel, Jr.

(10) Patent No.: US 10,012,574 B2
(45) Date of Patent: Jul. 3, 2018

(54) METHOD FOR METABOLOMIC SAMPLE PREPARATION BASED ON IONIC LIQUID DISPERSIVE LIQUID-LIQUID MICROEXTRACTION

(71) Applicant: Agilent Technologies, Inc., Loveland, CO (US)

(72) Inventor: James Alexander Apffel, Jr., Mountain View, CA (US)

(73) Assignee: Agilent Technologies, Inc., Santa Clara, CA (US)

(*) Notice: Subject to any disclaimer, the term of this patent is extended or adjusted under 35 U.S.C. 154(b) by 1033 days.

(21) Appl. No.: 14/205,100

(22) Filed: Mar. 11, 2014

(65) Prior Publication Data

US 2014/0273080 A1  Sep. 18, 2014

Related U.S. Application Data

(60) Provisional application No. 61/799,339, filed on Mar. 15, 2013.

(51) Int. Cl.
  *G01N 1/30* (2006.01)
  *G01N 33/50* (2006.01)
(52) U.S. Cl.
  CPC .......... *G01N 1/30* (2013.01); *G01N 33/5005* (2013.01); *G01N 2570/00* (2013.01)
(58) Field of Classification Search
  None
  See application file for complete search history.

(56) References Cited

U.S. PATENT DOCUMENTS 7,273,587 B1  9/2007  Birkner et al.
7,273,720 B1  9/2007  Birkner et al.
(Continued)

FOREIGN PATENT DOCUMENTS

WO  WO2007110637  10/2007
WO  WO2011155829  12/2011

OTHER PUBLICATIONS

Barbara Delgado, Veronica Pino, Jared L. Anderson, Juan H. Ayala, Ana M. Afonso, Venerando Gonzalez, An in-situ extraction-preconcentration method using ionic liquid-based surfactants for the determination of organic contaminants contained in marine sediments, 2012, Talanta, vol. 99, pp. 972-983.*

(Continued)

*Primary Examiner* — Renee Claytor
*Assistant Examiner* — Trent R Clarke
(74) *Attorney, Agent, or Firm* — Greer, Burns & Crain, Ltd.

(57) ABSTRACT

Provided herein is a method comprising one or more of the following steps: (a) lysing cells of a biological sample and contacting the biological sample with an amount of ionic liquid sufficient to denature intracellular metabolic enzymes in the biological sample to produce a contacted cellular sample; (b) mixing the contacted cellular sample with an organic solvent to produce an ionic liquid-organic solvent composition; (c) mixing the contacted cellular sample with the organic solvent to produce a dispersed microdroplet ionic liquid-organic solvent composition; (d) contacting the ionic liquid-organic solvent composition with an ion exchange composition to produce a second ionic liquid-organic solvent composition; (d) separating the ionic liquid from the organic solvent; and (e) extracting metabolites from the ionic liquid. Kits and systems for practicing the subject methods are also provided.

12 Claims, 4 Drawing Sheets

(56) References Cited

U.S. PATENT DOCUMENTS

| | | | |
|---|---|---|---|
| 8,143,381 B2 | 3/2012 | Von Hagen et al. | |
| 8,211,307 B2 | 7/2012 | Chew et al. | |
| 2009/0004048 A1 | 1/2009 | Elliott et al. | |
| 2011/0076748 A1* | 3/2011 | Salvo | C12N 1/06 435/257.1 |
| 2011/0124034 A1 | 5/2011 | Kuehnle et al. | |
| 2011/0192793 A1* | 8/2011 | Chew | C12N 1/06 210/633 |
| 2013/0109103 A1* | 5/2013 | Waldvogel | G01N 33/227 436/92 |

OTHER PUBLICATIONS

Jiaheng Zhang, Zhe Liang, Songqing Li, Yubo Li, Bing Peng, Wenfeng Zhou, Haixiang Gao, In-situ metathesis reaction combined with ultrasound-assisted ionic liquid dispersive liquid-liquid microextraction method for the determination of phenylurea pesticides in water samples, 2012, Talanta, vol. 98, pp. 145-151.*

Axel Schippers, Dagmar Kock, Carmen Höft, Gerrit Köweker and Michael Siegert , Quantification of microbial communities in subsurface marine sediments of the Black Sea and off Namibia, Frontiers in Microbiology, 2012, vol. 3, Article 16, pp. 1-11, published online Jan. 30, 2012.*

Lu, et al., "A Bioelectrochemical Method for the Quantitative Description of the Hofmeister Effect of Ionic Liquids in Aqueous Solution", J. Phys. Chem., 2012, 116, 11075-11080.

Rezaee, et al., "Determination of organic compounds in water using dispersive liquid-liquid microextraction", Journal of Chromatography A, 1116, 2006,1-9.

Shahriari, et al., "Role of the Hofmeister Series in the Formation of Ionic-Liquid-Based Aqueous Biphasic Systems", J. Phys. Chem., 2012, 116, 7252-7258.

Yao, et al., "Dispersive liquid-liquid microextraction using an in situ metathesis reaction to form an ionic liquid extraction phase for the preconcentration of aromatic compounds from water", Anal Bioanal Chem., 2009, 395:1491-1502.

* cited by examiner

METHOD FOR METABOLOMIC SAMPLE PREPARATION BASED ON IONIC LIQUID DISPERSIVE LIQUID-LIQUID MICROEXTRACTION

CROSS-REFERENCING

This patent application claims the benefit of U.S. provisional application Ser. No. 61/799,339, filed on Mar. 15, 2013, which application is incorporated by reference for all purposes.

BACKGROUND

Sample preparation is an analytical process which includes an extraction procedure that results in the isolation and enrichment of components of interest from a sample matrix. Extraction can vary in degree of selectivity, speed and convenience and depends not only on the approach and conditions used but also on the geometric configurations of the extraction phase. There is a constant need for the development of simplified and miniaturized sample preparation methods requiring lower quantities of purification materials and more efficient ways to obtain isolated and purified analytical samples.

SUMMARY

A method comprising: lysing cells of a biological sample; and contacting the biological sample with an amount of ionic liquid sufficient to denature intracellular metabolic enzymes in the biological sample to produce a contacted cellular sample is provided. In certain embodiments, the method comprises one or more of the following steps: (a) lysing cells of a biological sample and contacting the biological sample with an amount of ionic liquid sufficient to denature intracellular metabolic enzymes in the biological sample to produce a contacted cellular sample; (b) mixing the contacted cellular sample with an organic solvent to produce an ionic liquid-organic solvent composition; (c) mixing the contacted cellular sample with the organic solvent to produce a dispersed microdroplet ionic liquid-organic solvent composition; (d) contacting the ionic liquid-organic solvent composition with an ion exchange composition to produce a second ionic liquid-organic solvent composition; (d) separating the ionic liquid from the organic solvent; and (e) extracting metabolites from the ionic liquid. Kits and systems for practicing the subject methods are also provided.

BRIEF DESCRIPTION OF THE FIGURES

The skilled artisan will understand that the drawings, described below, are for illustration purposes only. The drawings are not intended to limit the scope of the present teachings in any way.

DEFINITIONS

Figure 1:
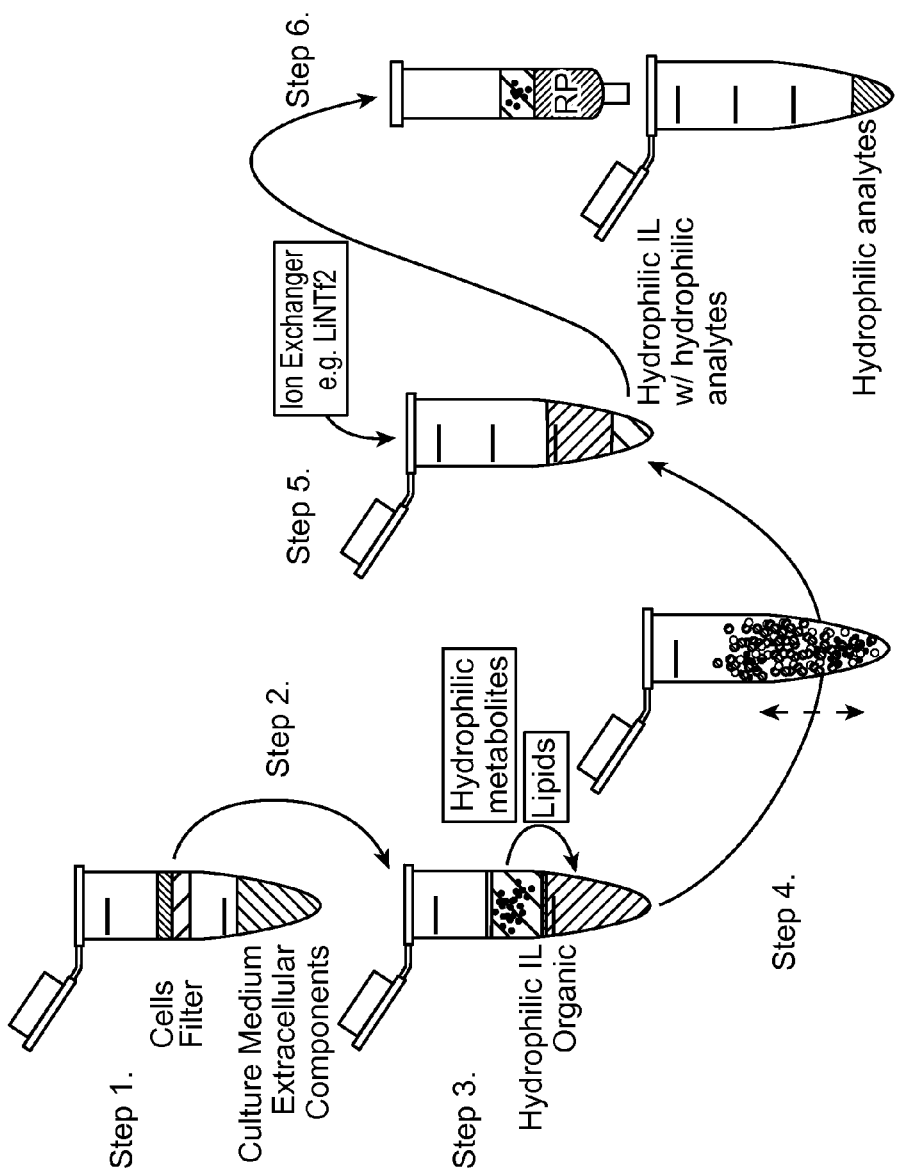
FIG. 1 schematically illustrates workflow for methods according one embodiment of the subject method.

Before describing exemplary embodiments in greater detail, the following definitions are set forth to illustrate and define the meaning and scope of the terms used in the description.

Unless defined otherwise, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with the general meaning of many of the terms used herein. Still, certain terms are defined below for the sake of clarity and ease of reference.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

The term "sample" as used herein relates to a material or mixture of materials, typically, although not necessarily, in liquid form, containing one or more analytes of interest. In one embodiment, the term as used in its broadest sense, refers to any plant, animal or bacterial material containing cells or producing cellular metabolites, such as, for example, tissue or fluid isolated from an individual (including without limitation plasma, serum, cerebrospinal fluid, lymph, tears, saliva and tissue sections) or from in vitro cell culture constituents, as well as samples from the environment. The term "sample" may also refer to a "biological sample". As used herein, the term "a biological sample" refers to a whole organism or a subset of its tissues, cells or component parts (e.g. body fluids, including but not limited to blood, mucus, lymphatic fluid, synovial fluid, cerebrospinal fluid, saliva, amniotic fluid, amniotic cord blood, urine, vaginal fluid and semen). A "biological sample" can also refer to a homogenate, lysate or extract prepared from a whole organism or a subset of its tissues, cells or component parts, or a fraction or portion thereof, including but not limited to, for example, plasma, serum, spinal fluid, lymph fluid, the external sections of the skin, respiratory, intestinal, and genitourinary tracts, tears, saliva, milk, blood cells, tumors, organs. In certain embodiments, the sample has been removed from an animal or plant. Biological samples of the invention include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The term "denaturing," as used herein, refers to the process in which proteins or nucleic acids lose tertiary and secondary structure which is present in the native state by the application of some external stress or compound, such as an acid or base, a concentrated inorganic salt, an organic solvent or heat. Protein denaturation includes enzyme denaturation where quaternary denaturation includes protein subunits being dissociated or the spatial arrangement of protein subunits being disrupted. Protein denaturation may further include tertiary structure denaturation which includes the disruption of covalent interactions between amino acid side chains (such as disulfide bridges between cysteine groups), non-covalent dipole-dipole interactions between polar amino acid side chains and surrounding media, Van der Waals interactions (e.g., induced dipole moments) between non-polar amino acid side chains. Protein denaturation may further include secondary structure denaturation where proteins, including enzymes lose all regular repeating patterns such as alpha-helices and beta-pleated sheets and may adopt a random-coil type configuration. Protein denaturation does not disrupt or change covalent peptide bonds or the sequence of amino acids held together (i.e., does not disrupt primary structure).

The terms "determining", "measuring", "evaluating", "assessing," "assaying," and "analyzing" are used interchangeably herein to refer to any form of measurement, and include determining if an element is present or not. These terms include both quantitative and/or qualitative determinations. Assessing may be relative or absolute. "Assessing the presence of" includes determining the amount of something present, as well as determining whether it is present or absent.

The term "using" has its conventional meaning, and, as such, means employing, e.g., putting into service, a method or composition to attain an end. For example, if a program is used to create a file, a program is executed to make a file, the file usually being the output of the program. In another example, if a computer file is used, it is usually accessed, read, and the information stored in the file employed to attain an end. Similarly if a unique identifier, e.g., a barcode is used, the unique identifier is usually read to identify, for example, an object or file associated with the unique identifier.

Furthermore, except as otherwise noted, the chemical methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Where compounds described herein contain one or more chiral centers and/or double-bond isomers (i.e., geometric isomers), enantiomers or diastereomers, all possible enantiomers and stereoisomers of the compounds including the stereoisomerically pure form (e.g., geometrically pure, enantiomerically pure or diastereomerically pure) and enantiomeric and stereoisomeric mixtures are included in the description of the compounds herein. Enantiomeric and stereoisomeric mixtures can be resolved into their component enantiomers or stereoisomers using separation techniques or chiral synthesis techniques well known to the skilled artisan. The compounds can also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that can be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Compounds can exist in unsolvated forms as well as solvated forms, including hydrated forms. In general, compounds can be hydrated or solvated. Certain compounds can exist in multiple crystalline or amorphous forms. In general, all physical forms are equivalent for the uses contemplated herein and are intended to be within the scope of the present disclosure.

As used herein, the term "alkyl" by itself or as part of another substituent refers to a saturated branched or straight-chain monovalent hydrocarbon radical derived by the removal of one hydrogen atom from a single carbon atom of a parent alkane. Typical alkyl groups include, but are not limited to, methyl; ethyl, propyls such as propan-1-yl or propan-2-yl; and butyls such as butan-1-yl, butan-2-yl, 2-methyl-propan-1-yl or 2-methyl-propan-2-yl. In some embodiments, an alkyl group comprises from 1 to 20 carbon atoms. In other embodiments, an alkyl group comprises from 1 to 10 carbon atoms. In still other embodiments, an alkyl group comprises from 1 to 6 carbon atoms, such as from 1 to 4 carbon atoms.

"Alkanyl" by itself or as part of another substituent refers to a saturated branched, straight-chain or cyclic alkyl radical derived by the removal of one hydrogen atom from a single carbon atom of an alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkylene" refers to a branched or unbranched saturated hydrocarbon chain, usually having from 1 to 40 carbon atoms, more usually 1 to 10 carbon atoms and even more usually 1 to 6 carbon atoms. This term is exemplified by groups such as methylene (—$CH_2$—), ethylene (—$CH_2CH_2$—), the propylene isomers (e.g., —$CH_2CH_2CH_2$— and —$CH(CH_3)CH_2$—) and the like.

"Alkenyl" by itself or as part of another substituent refers to an unsaturated branched, straight-chain or cyclic alkyl radical having at least one carbon-carbon double bond derived by the removal of one hydrogen atom from a single carbon atom of an alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl" by itself or as part of another substituent refers to an unsaturated branched, straight-chain or cyclic alkyl radical having at least one carbon-carbon triple bond derived by the removal of one hydrogen atom from a single carbon atom of an alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Acyl" by itself or as part of another substituent refers to a radical —C(O)R$^{30}$, where R$^{30}$ is hydrogen, alkyl, cycloalkyl, cycloheteroalkyl, aryl, arylalkyl, heteroalkyl, heteroaryl, heteroarylalkyl as defined herein and substituted versions thereof. Representative examples include, but are not limited to formyl, acetyl, cyclohexylcarbonyl, cyclohexylmethylcarbonyl, benzoyl, benzylcarbonyl, piperonyl, succinyl, and malonyl, and the like.

The term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Alkoxy" by itself or as part of another substituent refers to a radical —OR$^{31}$ where R$^{31}$ represents an alkyl or cycloalkyl group as defined herein. Representative examples include, but are not limited to, methoxy, ethoxy, propoxy, butoxy, cyclohexyloxy and the like.

"Alkoxycarbonyl" by itself or as part of another substituent refers to a radical —C(O)OR$^{31}$ where R$^{31}$ represents an alkyl or cycloalkyl group as defined herein. Representative examples include, but are not limited to, methoxycarbonyl, ethoxycarbonyl, propoxycarbonyl, butoxycarbonyl, cyclohexyloxycarbonyl and the like.

"Aryl" by itself or as part of another substituent refers to a monovalent aromatic hydrocarbon radical derived by the removal of one hydrogen atom from a single carbon atom of an aromatic ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In certain embodiments, an aryl group comprises from 6 to 20 carbon atoms. In certain embodiments, an aryl group comprises from 6 to 12 carbon atoms. Examples of an aryl group are phenyl and naphthyl.

"Arylalkyl" by itself or as part of another substituent refers to an acyclic alkyl radical in which one of the hydrogen atoms bonded to a carbon atom, typically a terminal or sp$^3$ carbon atom, is replaced with an aryl group. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In certain embodiments, an arylalkyl group is (C$_7$-C$_{30}$) arylalkyl, e.g., the alkanyl, alkenyl or alkynyl moiety of the arylalkyl group is (C$_1$-C$_{10}$) and the aryl moiety is (C$_6$-C$_{20}$). In certain embodiments, an arylalkyl group is (C$_7$-C$_{20}$) arylalkyl, e.g., the alkanyl, alkenyl or alkynyl moiety of the arylalkyl group is (C$_1$-C$_8$) and the aryl moiety is (C$_6$-C$_{12}$).

"Arylaryl" by itself or as part of another substituent, refers to a monovalent hydrocarbon group derived by the removal of one hydrogen atom from a single carbon atom of a ring system in which two or more identical or non-identical aromatic ring systems are joined directly together by a single bond, where the number of such direct ring junctions is one less than the number of aromatic ring systems involved. Typical arylaryl groups include, but are not limited to, biphenyl, triphenyl, phenyl-napthyl, binaphthyl, biphenylnapthyl, and the like. When the number of carbon atoms in an arylaryl group are specified, the numbers refer to the carbon atoms comprising each aromatic ring. For example, (C$_5$-C$_{14}$) arylaryl is an arylaryl group in which each aromatic ring comprises from 5 to 14 carbons, e.g., biphenyl, triphenyl, binaphthyl, phenylnapthyl, etc. In certain embodiments, each aromatic ring system of an arylaryl group is independently a (C$_5$-C$_{14}$) aromatic. In certain embodiments, each aromatic ring system of an arylaryl group is independently a (C$_5$-C$_{10}$) aromatic. In certain embodiments, each aromatic ring system is identical, e.g., biphenyl, triphenyl, binaphthyl, trinaphthyl, etc.

"Cycloalkyl" by itself or as part of another substituent refers to a saturated or unsaturated cyclic alkyl radical. Where a specific level of saturation is intended, the nomenclature "cycloalkanyl" or "cycloalkenyl" is used. Typical cycloalkyl groups include, but are not limited to, groups derived from cyclopropane, cyclobutane, cyclopentane, cyclohexane and the like. In certain embodiments, the cycloalkyl group is (C$_3$-C$_{10}$) cycloalkyl. In certain embodiments, the cycloalkyl group is (C$_3$-C$_7$) cycloalkyl.

"Cycloheteroalkyl" or "heterocyclyl" by itself or as part of another substituent, refers to a saturated or unsaturated cyclic alkyl radical in which one or more carbon atoms (and any associated hydrogen atoms) are independently replaced with the same or different heteroatom. Typical heteroatoms to replace the carbon atom(s) include, but are not limited to, N, P, O, S, Si, etc. Where a specific level of saturation is intended, the nomenclature "cycloheteroalkanyl" or "cycloheteroalkenyl" is used. Typical cycloheteroalkyl groups include, but are not limited to, groups derived from epoxides, azirines, thiiranes, imidazolidine, morpholine, piperazine, piperidine, pyrazolidine, pyrrolidine, quinuclidine and the like.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$—, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or $sp^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

"Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexylene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Substituted" refers to a group in which one or more hydrogen atoms are independently replaced with the same or different substituent(s). Typical substituents include, but are not limited to, alkylenedioxy (such as methylenedioxy), -M, —$R^{60}$, —$O^-$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2O^-$, —$S(O)_2OH$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$C(S)OR^{60}$, —$NR^{62}C(O)NR^{60}R^{61}$, —$NR^{62}C(S)NR^{60}R^{61}$, —$NR^{62}C(NR^{63})NR^{60}R^{61}$ and —$C(NR^{62})NR^{60}R^{61}$ where M is halogen; $R^{60}$, $R^{61}$, $R^{62}$ and $R^{63}$ are independently hydrogen, alkyl, substituted alkyl, alkoxy, substituted alkoxy, cycloalkyl, substituted cycloalkyl, cycloheteroalkyl, substituted cycloheteroalkyl, aryl, substituted aryl, heteroaryl or substituted heteroaryl, or optionally $R^{60}$ and $R^{61}$ together with the nitrogen atom to which they are bonded form a cycloheteroalkyl or substituted cycloheteroalkyl ring; and $R^{64}$ and $R^{65}$ are independently hydrogen, alkyl, substituted alkyl, aryl, cycloalkyl, substituted cycloalkyl, cycloheteroalkyl, substituted cycloheteroalkyl, aryl, substituted aryl, heteroaryl or substituted heteroaryl, or optionally $R^{64}$ and $R^{65}$ together with the nitrogen atom to which they are bonded form a cycloheteroalkyl or substituted cycloheteroalkyl ring. In certain embodiments, substituents include -M, —$R^{60}$, =O, —$OR^{60}$, —$SR^{60}$, —$S^-$, =S, —$NR^{60}R^{61}$, =$NR^{60}$, —$CF_3$, —CN, —OCN, —SCN, —NO, —$NO_2$, =$N_2$, —$N_3$, —$S(O)_2R^{60}$, —$OS(O)_2O^-$, —$OS(O)_2R^{60}$, —$P(O)(O^-)_2$, —$P(O)(OR^{60})(O^-)$, —$OP(O)(OR^{60})(OR^{61})$, —$C(O)R^{60}$, —$C(S)R^{60}$, —$C(O)OR^{60}$, —$C(O)NR^{60}R^{61}$, —$C(O)O^-$, —$NR^{62}C(O)NR^{60}R^{61}$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$P(O)(OR^{60})(O^-)$, —$OP(O)(OR^{60})(OR^{61})$, —$C(O)R^{60}$, —$C(O)OR^{60}$, —$C(O)NR^{60}R^{61}$, —$C(O)O^-$. In certain embodiments, substituents include -M, —$R^{60}$, =O, —$OR^{60}$, —$SR^{60}$, —$NR^{60}R^{61}$, —$CF_3$, —CN, —$NO_2$, —$S(O)_2R^{60}$, —$OP(O)(OR^{60})(OR^{61})$, —$C(O)R^{60}$, —$C(O)OR^{60}$, —$C(O)O^-$, where $R^{60}$, $R^{61}$ and $R^{62}$ are as defined above. For example, a substituted group may bear a methylenedioxy substituent or one, two, or three substituents selected from a halogen atom, a (1-4C)alkyl group and a (1-4C)alkoxy group.

A "plurality" contains at least 2 members. In certain cases, a plurality may have at least 10, at least 100, at least 100, at least 10,000, at least 100,000, at least $10^6$, at least $10^7$, at least $10^8$ or at least $10^9$ or more members.

Numeric ranges are inclusive of the numbers defining the range.

The term "separating", as used herein, refers to physical separation of two elements (e.g., by size or affinity, etc.) as well as degradation of one element, leaving the other intact.

The methods described herein include multiple steps. Each step may be performed after a predetermined amount of time has elapsed between steps, as desired. As such, the time between performing each step may be 1 second or more, 10 seconds or more, 30 seconds or more, 60 seconds or more, 5 minutes or more, 10 minutes or more, 60 minutes or more and including 5 hours or more. In certain embodiments, each subsequent step is performed immediately after completion of the previous step. In other embodiments, a step may be performed after an incubation or waiting time after completion of the previous step, e.g., a few minutes to an overnight waiting time.

Other definitions of terms may appear throughout the specification.

DESCRIPTION OF EXEMPLARY EMBODIMENTS

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

In further describing the subject invention, methods for extracting and purifying compounds from a biological sample having cells using an ionic liquid are described first in greater detail. Next, ionic liquids of interest for practicing the subject methods are reviewed. Systems and kits are also described.

Methods for Extracting and Purifying Compounds from a Biological Sample Having Cells As summarized above, aspects of the invention include methods for extracting and purifying compounds from a biological sample comprising cells. The phrase "extracting and purifying" is used in its conventional sense to refer to isolating desired compounds (e.g., metabolites) from a plurality of components in a biological sample having cells.

In certain embodiments, compounds extracted by the subject methods are metabolites. The term "metabolites" is used herein its conventional sense to refer to one or more compounds found which are the substrates or products of metabolic process which occur within a cell. As such, metabolites may include substrates or products which are produced by metabolic processes including, but not limited to glycolysis, tricarboxylic acid cycle (i.e., TCA cycle, Krebs cycle), reductive pentose phosphate cycle (i.e., Calvin cycle), glycogen metabolism, pentose phosphate pathway, among other metabolic processes. Accordingly, metabolites of interest may include but are not limited to glucose, glucose-6-phosphate, fructose-6-phosphate, fructose-1,6-phosphate, glyceraldehyde 3-phosphate, dihydroxyacetone phosphate, 1,3-bisphosphoglycerate, 3-phosphoglycerate, 2-phosphoglycerate, phosphoenolpyruvate, pyruvate, acetyl CoA, citrate, cis-aconitate, d-isocitrate, α-ketoglutarate, succinyl CoA, succinate, fumarate, malate, oxaloacetate, ribulose 1,5-bisphosphate, 3-phosphoglycerate, 1,3-bisphosphoglycerate, glyceraldehyde 3-phosphate, ribulose-5-phosphate, ethanol, acetylaldehyde, pyruvic acid, 6-phosphogluconolactone, 6-phosphogluconate, ribose-5-phosphate, xylulose-5-phosphate, sedoheptulose 7-phosphate, erythrose 4-phosphate, among other metabolites.

In embodiments of the invention, methods for extracting and purifying metabolites from a biological sample having cells are provided. The term "biological sample" is used herein to refer to a whole organism, plant, fungi or a subset of animal tissues, cells or component parts which may in certain instances be found in blood, mucus, lymphatic fluid, synovial fluid, cerebrospinal fluid, saliva, amniotic fluid, amniotic cord blood, urine, vaginal fluid and semen. As such, a "biological sample" used herein can refer to a homogenate, lysate or extract prepared from a whole organism or a subset of its tissues, including but not limited to, for example, plasma, serum, spinal fluid, lymph fluid, the external sections of the skin, respiratory, intestinal, and genitourinary tracts, tears, saliva, milk, blood cells, tumors, organs. In embodiments of the invention, a "biological sample" will contain cells from the animal, plants, bacteria or fungi. A "biological sample" can also refer to a medium, such as a nutrient broth or gel in which an organism has been propagated, which contains cells as well as cellular components, such as proteins or nucleic acid molecules. Biological samples of the invention include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

Aspects of the invention include lysing cells of a biological sample and contacting the biological sample with an amount of ionic liquid sufficient to denature intracellular metabolic enzymes in the biological sample. By "lyse" cells is meant that the cells are ruptured or broken open such that the internal contents of the cells, including metabolic enzymes are released into the surrounding medium (e.g., ionic liquid). In some embodiments, cell lysis may further include lysis of cellular organelles, for example the nucleus, mitochondria, ribosomes, chloroplasts, lysosomes, vacuoles, Golgi apparatus, centrioles, etc. such that the contents of the cellular organelles are also released into the surrounding medium.

In some embodiments, lysing the cells of a biological sample is performed by contacting the cells of the biological sample with a lysing agent. The lysing agent may be any suitable lysing agent so long as it is sufficient to break open the cells where that the internal contents of the cell are released into the surrounding medium. The lysing agent may be contacted with the biological sample having the cells at the same time (i.e., simultaneously) as contacting the biological sample having cells with ionic liquid. Alternatively, the lysing agent may be contacted with the biological sample sufficient to break open the cells before contacting the sample with the ionic liquid. In other words, in these embodiments, the biological sample having cells that is contacted with the ionic liquid includes cells which have been previously broken open by one or more lysing agents. In certain embodiments, the ionic liquid functions as the lysing agent and contacting the biological sample having cells with the ionic liquid is sufficient to lyse the cells of the sample and denature intracellular metabolic enzymes without the need for an additional lysing agent. In these embodiments, aspects of the invention include contacting a biological sample having cells with an amount of ionic liquid sufficient to lyse the cells and denature intracellular metabolic enzymes in the biological sample.

As described in greater detail below, intracellular enzymes are denatured by contacting with the ionic liquid. The term "denature" is used in its conventional sense to mean that the structural conformation of the subject proteins or enzymes is destabilized or disrupted, in certain embodiments the proteins or enzymes losing quaternary, tertiary and secondary structure that is otherwise present in its native state. Protein denaturation by the ionic liquid includes quaternary denaturation where protein sub-units are dissociated or the spatial arrangement of protein subunits is disrupted. Protein denaturation by ionic liquids may further include tertiary structure denaturation which includes the disruption of covalent interactions between amino acid side chains (such as disulfide bridges between cysteine groups), non-covalent dipole-dipole interactions between polar amino acid side chains and surrounding media, Van der Waals interactions (e.g., induced dipole moments) between non-polar amino acid side chains. Protein denaturation by ionic liquids may further include secondary structure denaturation where the proteins or enzymes lose all regular repeating patterns such as alpha-helices and beta-pleated sheets and may adopt a random-coil type configuration. In embodiments of the invention, the biological sample having cells is contacted at room temperature (i.e., about 20° C. or 68° F. or 293K)

Where compounds extracted and purified by the subject methods include metabolites, ionic liquids of interest include those sufficient to destabilize, disrupt or denature metabolic enzymes. Metabolic enzymes may include, but are not limited to those employed in the metabolic processes discussed above, such as metabolic enzymes in glycolysis, tricarboxylic acid cycle (i.e., TCA cycle, Krebs cycle), reductive pentose phosphate cycle (i.e., Calvin cycle), glycogen metabolism, the pentose phosphate pathway, among other metabolic processes. For example, metabolic enzymes may include, but are not limited to: hexokinase, phosphoglucose isomerase, phosphofructokinase, fructose bisphosphate aldolase, triose phosphate isomerase, glyceraldehyde phosphate dehydrogenase, phophoglycerate kinase, phosphoglycerate mutase, enolase, pyruvate kinase, pyruvate dehydrogenase, citrate synthase, aconitase, isocitrate dehydrogenase, α-ketoglutarate dehydrogenase, succinyl-CoA synthetase, succinic dehydrogenase, fumarase, malate dehydrogenase, pyruvate carboxylase, ribulose-1,5-bisphophate carboxylase oxygenase, glyceraldehyde 3-phosphate dehydrogenase, phosphopentose epimerase, phosphoribulokinase, glucose-6-phosphate dehydrogenase, gluconolactonase, 6-phosphogluconate dehydrogenase, ribulose-5-phosphate isomerase, ribulose-5-phosphate 3-epimerase, transaldolase, transketolase, among other metabolic pathway enzymes.

Contacting the biological sample having cells with the ionic liquid may include mixing the cells in the ionic liquid. Any convenient method may be employed to stir the biological sample having cells with the ionic liquid, so long as the cells are sufficiently mixed throughout and in contact with the ionic liquid. Mixing may include, for example stirring with a magnetic stir bar or manually stirred using any convenient stirring apparatus. Alternatively, the biological sample in the ionic liquid may be stirred by vortexing the contacted sample, shaking the contacted sample such as with a mechanical shaker or shaking may be manually performed (i.e., by hand). In yet other instances, mixing the biological sample having cells with the ionic liquid includes sonicating the contacted composition.

As described above, methods include contacting a biological sample having cells with an ionic liquid. The term "ionic liquid" is used in its conventional sense to refer to a salt in liquid state. Ionic liquids of interest are compounds in the liquid state at room temperature that are made of ions or short-lived ion pairs and may alternatively be referred to by one of ordinary skill in the art as liquid electrolytes, ionic melts, ionic fluids, fused salts, liquid salts or ionic glasses. As such, ionic liquids according to embodiments of the invention are salts composed of ion pairs that are in the liquid state at room temperature. As noted above, ionic liquids of the invention destabilize, disrupt or denature enzyme structure. Any convenient ionic liquid may be employed in the subject methods so long as the ionic liquid destabilizes, disrupts and/or denatures enzyme structure. In certain embodiments, the ionic liquid is hydrophilic. In other embodiments, the ionic liquid is hydrophobic.

In certain embodiments, the ionic liquid includes a cation selected from the group consisting of:

a)

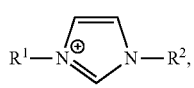

Formula (I)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or b)

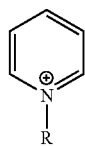

Formula (II)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or c)

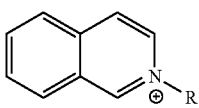

Formula (III)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or d)

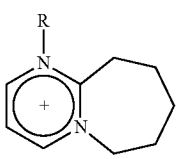

Formula (IV)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or e)

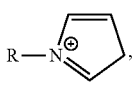

Formula (V)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or f)

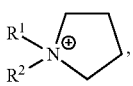

Formula (VI)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl.

In certain embodiments, the ionic liquid includes a cation having Formula (I):

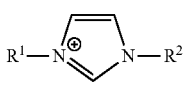

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl. In some instances, $R^1$ is methyl and $R^2$ is butyl. In certain embodiments, ionic liquids of interest include 1-butyl-3-methyl-imidazol-3-ium.

In some embodiments, the ionic liquid includes a cation selected from the group consisting of sulfonium cations, phosphonium cations, tetraalkyl ammonium cations and pyrazolium cations. In other embodiments, the ionic liquid is a compound selected from the group consisting of 1,2,4-trimethylpyrazolium methylsulfate, methyl-trioctylammonium bis(trifluoromethylsulfonyl)imide, trihexyltetradecylphosphonium bromide and 5-(trifluoromethyl)dibenzothiophenium trifluoromethanesulfonate.

Contacting the biological sample having cells with an ionic liquid lyses the cells, releasing the cellular components into the ionic liquid and denatures the metabolic enzymes found within the cells. As such, contacting the biological sample having cells according to the subject methods quenches metabolic processes of the cell upon contact/mixing with the ionic liquid. By "quenches" metabolic processes is meant that metabolic processes which occur in the native cell are stopped by lysis and denaturation. As such, in practicing methods of the invention, 95% or more of metabolic process in the cell are quenched after contacting the biological sample with the ionic liquid, such as 97% or more, such as 99% or more, such as 99.5% or more, such as 99.9% or more, and including all of the metabolic processes mediated by enzymes are quenched by lysis and denaturation of metabolic enzymes by contacting with the ionic liquids.

After contacting the biological sample with the ionic liquid, the cellular sample is mixed with an organic solvent. In certain embodiments, the organic solvent may be added to the ionic liquid cellular sample to form an ionic liquid cellular sample-organic solvent two phase composition. By "two phase" composition is meant that the ionic liquid cellular sample is not miscible with the organic solvent and form two distinct layers. As such, in these embodiments, the organic solvent and ionic liquids are not miscible. For example, where the ionic liquid is hydrophilic, the organic solvent may be hydrophobic. Likewise, where the ionic liquid is hydrophobic, the organic solvent may be hydrophilic. In certain embodiments where a two-phase composition is formed, the organic liquid is denser than the ionic liquid. In other words, after addition of the organic solvent to the ionic liquid, the organic phase is positioned at the bottom of the two-phase composition and the ionic liquid cellular sample phase is positioned on top.

In some embodiments, the organic liquid mixed with the ionic liquid cellular sample is a hydrophobic or non-polar organic solvent. Hydrophobic or non-polar organic solvents of interest include, but are not limited to pentane, hexane, heptane, octane, diethyl ether, and chloroform. Where a hydrophobic or non-polar organic solvent is employed, non-polar and hydrophobic cellular components will be extraced into the organic solvent layer. As such, the hydrophobic cellular components (e.g., lipids, nonpolar membrane components, etc.) from the ionic liquid cellular sample will be extracted into the organic phase of the two phase composition.

In certain embodiments, a dispersed microdroplet composition is produced after mixing an organic liquid with the ionic liquid cellular sample. The term "microdroplet" is used in its conventional sense to refer to aggregates of the ionic liquid cellular sample composition within the organic solvent medium having dimensions ranging from 0.001 μm to 1000 μm such as 0.01 μm to 100 μm, such as 0.1 μm to 10

μm and including 1 μm. By forming the microdroplets, the surface area of the ionic liquid cellular sample is increased, where in certain instances the hydrophobic components in the ionic liquid cellular sample are extracted into the organic solvent medium. Likewise, by forming a dispersed microdroplet composition, the proteins and enzymes denatured by contacting with the ionic liquid precipitate. Remaining in the ionic liquid phase are the subject compounds, e.g., metabolites.

Microdroplet dispersions may be formed by any convenient protocol, so long as the ionic liquid cellular sample-organic solvent composition is agitated sufficient to form dispersed microdroplets of ionic liquid cellular sample in organic solvent medium. In certain embodiments, agitation may result in turbid solutions having a plurality of microdroplets homogeneously dispersed throughout the organic solvent. Agitation may include, but is not limited to vortexing the composition, sonicating the composition, shaking the composition either manually (i.e., by hand) or mechanically (i.e., by a mechanically or electrically powered shaking device), rapidly stirring the composition manually, among other agitating protocols. Agitation may be performed for any amount of time, so long as agitation is sufficient to produce the desired microdroplet dispersions. As such, agitation may be performed for one second or longer, such as for two seconds or longer, such as for 5 seconds or longer, such as for 10 seconds or longer, such as for 30 seconds or longer, such as for 1 minute or longer, such as for 5 minutes or longer, such as for 10 minutes or longer and including agitation for 30 minutes or longer.

In certain embodiments, a dispersant is not added to produce the microdroplet dispersions. As such, in these embodiments no additional compounds are added in order to create the microdroplet dispersions other than agitation of the sample.

In the subject methods, the dispersed microdroplet composition may be subsequently contacted with an ion exchange composition to produce an ionic liquid-organic solvent two phase composition where the ionic liquid exchanges cations with the ion exchange composition in a salt metathesis reaction. The term salt "metathesis" reaction is used in its conventional sense to refer to the transposition chemical process involving the exchange of bonds between two ionic species which result in the exchanging of counterions between the two salts. In other words, the subject ionic liquid will undergo a metathesis reaction with the added salt to exchange counterion forming two new distinct salt compounds. This reaction may be represented generally by generic scheme 1 below:

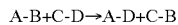

A-B+C-D→A-D+C-B    (Scheme 1)

In some embodiments, the ion exchange composition is a second ionic liquid. In certain instances, the ion exchange composition includes a salt having an anion selected from the group consisting of boron tetrafluoride, bis-(2,4,4-trimethylpentyl)phosphinate, bis-(trifluoromethyl)imide, bis[(trifluoromethane)sulfonyl]imide, bis-(trifluoromethylsulfonyl)methane, bis-biphenyldiolatoborate, bis-malonatoborate, bis-oxalatoborate, bis-(pentafluoroethyl)phosphinate, bis-salicylatoborate, bromine, butylsulfate, chloride, perchlorate, decanoate, dicyanamide, ethylsulfate, iodide, methylsulfate, octylsulfate, hexafluorophosphate, tetracyanoborate, toluene-4-sulfonate, trifluoromethane-sulfonate, tris-(nonafluorobutyl)-trifluorophosphate and tris-(pentafluoroethyl)trifluorophosphate. As such, the subject ionic liquid from the dispersed microdroplet composition will exchange anions with the ion exchange composition to form a new salt having an anion that is one or more of boron tetrafluoride, bis-(2,4,4-trimethylpentyl)phosphinate, bis-(trifluoromethyl)imide, bis[(trifluoromethane)sulfonyl]imide, bis-(trifluoromethylsulfonyl)methane, bis-biphenyldiolatoborate, bis-malonatoborate, bis-oxalatoborate, bis-(pentafluoroethyl)phosphinate, bis-salicylatoborate, bromine, butylsulfate, chloride, perchlorate, decanoate, dicyanamide, ethylsulfate, iodide, methylsulfate, octylsulfate, hexafluorophosphate, tetracyanoborate, toluene-4-sulfonate, trifluoromethane-sulfonate, tris-(nonafluorobutyl)-trifluorophosphate and tris-(pentafluoroethyl)trifluorophosphate. In certain embodiments, the ion exchange composition includes lithium bis[(trifluoromethane)sulfonyl]imide (LiNTf$_2$) and the anion exchange with the ionic liquid of the dispersed microdroplets includes the formation of a new ionic salt having a bis[(trifluoromethane)sulfonyl]imide (NTf$_2$) anion.

In embodiments of the invention, the addition of the ion exchange composition to the dispersed microdroplet composition is sufficient to form an ionic liquid cellular sample-organic solvent two phase composition. As noted above, the two phase composition includes an ionic liquid composition that is not miscible with the organic solvent and thus, forms two distinct layers. By contacting the dispersed microdroplet composition with the ion exchange composition, the organic layer and ionic liquid layers can be separated. In certain embodiments, the newly formed ionic liquid with exchanged anion is denser than the organic solvent layer. In other words, after addition of the ion exchange composition to the dispersed microdroplet composition, the organic solvent phase is positioned at the top of the two-phase composition and the ionic liquid phase is positioned on the bottom.

After formation of distinct layers in an ionic liquid-organic solvent two-phase composition, the ionic liquid may be separated from the organic solvent. The ionic liquid may be separated from the organic layer by any convenient protocol, including but not limited pouring off the organic solvent, aspirating to separate the ionic liquid from the organic solvent (e.g., using either a manual, mechanically controlled, hydraulically controlled or electrically controlled pipet) or by evaporation of the organic solvent (e.g., vacuum evaporation, by bubbling inert gas through the organic phase).

Methods of the invention may further include separating the target compounds (e.g., metabolites) extracted from the biological sample cells from the ionic liquid, such as for example by microextraction. Microextraction protocols of interest may be any convenient microextraction so long as the protocol is sufficient to extract the target metabolites from the ionic liquids. For example, microextraction may include solid phase chromatography. In certain embodiments, solid phase chromatography includes, but is not limited to ion exchange chromatography, liquid chromatography employing a reverse phase stationary column, among other chromatography protocols.

In some embodiments, separating the metabolites from the ionic liquid further includes analysis of the separated metabolites. By analyzed is meant characterizing the chemical composition of the separated metabolites, including but not limited to the amount and types of compounds in the extracted metabolites as well as any impurities present. Chemical analysis may be conducted using any convenient protocol, such as for example by mass spectrometry, infrared spectroscopy, UV-vis spectroscopy, colorimetry and nuclear magnetic resonance spectroscopy. In certain embodiments, chemical analysis is conducted by gas chromatography-mass spectrometry. In other embodiments, chemical analysis is conducted by liquid chromatography-mass spectrometry.

As described above, methods of the present disclosure may include analyzing the separated metabolite compositions by liquid chromatography-mass spectrometry systems. For example, the apparatus may include analytical separation device such as a liquid chromatograph (LC), including a high performance liquid chromatograph (HPLC), a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, a the subject sample may be applied to the LC-MS system by employing a nano- or micropump in certain embodiments.

Mass spectrometer systems for use in the subject methods may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. Such systems are well known in the art (see, e.g., U.S. Pat. Nos. 7,534,996, 7,531,793, 7,507,953, 7,145,133, 7,229,834 and 6,924,478) and may be implemented in a variety of configurations. In certain embodiments, tandem mass spectrometry may be done using individual mass analyzers that are separated in space or, in certain cases, using a single mass spectrometer in which the different selection steps are separated in time. Tandem MS "in space" involves the physical separation of the instrument components (QqQ or QTOF) whereas a tandem MS "in time" involves the use of an ion trap.

An example mass spectrometer system may contain an ion source containing an ionization device, a mass analyzer and a detector. As is conventional in the art, the ion source and the mass analyzer are separated by one or more intermediate vacuum chambers into which ions are transferred from the ion source via, e.g., a transfer capillary or the like. Also as is conventional in the art, the intermediate vacuum chamber may also contain a skimmer to enrich analyte ions (relative to solvent ions and gas) contained in the ion beam exiting the transfer capillary prior to its entry into the ion transfer optics (e.g., an ion guide, or the like) leading to a mass analyzer in high vacuum.

The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multi-mode" ionization source). In one embodiment, the precursor ions may be made by EI, ESI or MALDI, and a selected precursor ion may be fragmented by collision or using photons to produce product ions that are subsequently analyzed.

Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

Ionic liquids are suitable for denaturing proteins and have been used for the extraction of small molecules and DNA. Using an ionic liquid, the entire cellular contents of a biological sample can be solubilized and denatured. By denaturing the proteins, the degradation of DNA and RNA can be significantly reduced. In one embodiment, an ionic liquid can be used to solubilize the entire contents of a biological sample, denature proteins, DNA, and RNA, and separate each individual component from the mixture.

The denaturation process can be instantaneous when a large amount of ionic liquid is introduced to the sample (e.g., at least 2×, at least 5× or at least 10×, by volume). After addition of the ionic liquid, proteins can be removed from the sample, e.g., via an amine reactive moiety that is attached to a solid phase. By removing the protein from the sample, the remaining components are much less susceptible to degradation. In certain cases, a cleavable linker can be attached to the solid phase so that the proteins can be released from the solid phase and later analyzed by mass spectrometry.

Following removal of the proteins, an ion-exchange reaction can be induced by adding, e.g., lithium bis(trifluoromethanesulfonimide) (LiNTf2). The aqueous layer produced in this reaction is free of hydrophobic species such as lipids. RNA and glycans can then be separated from DNA by oxidation of the 3' terminus that contains a 2', 3' diol to aldehydes (or cis diols for carbohydrates) and capture by hydrazide beads. The beads containing RNA and/or glycans can later be released and analyzed. The remaining aqueous layer contains only DNA and hydrophilic small molecules, which can readily be separated (if necessary) by size exclusion chromatography and analyzed.

All steps of this process are fast and efficient. Although the purity of the components may not be extremely high, removal of specific components such as proteins may allow a much faster workflow to obtain the species desired, such as DNA for PCR reactions.

Figure 4:
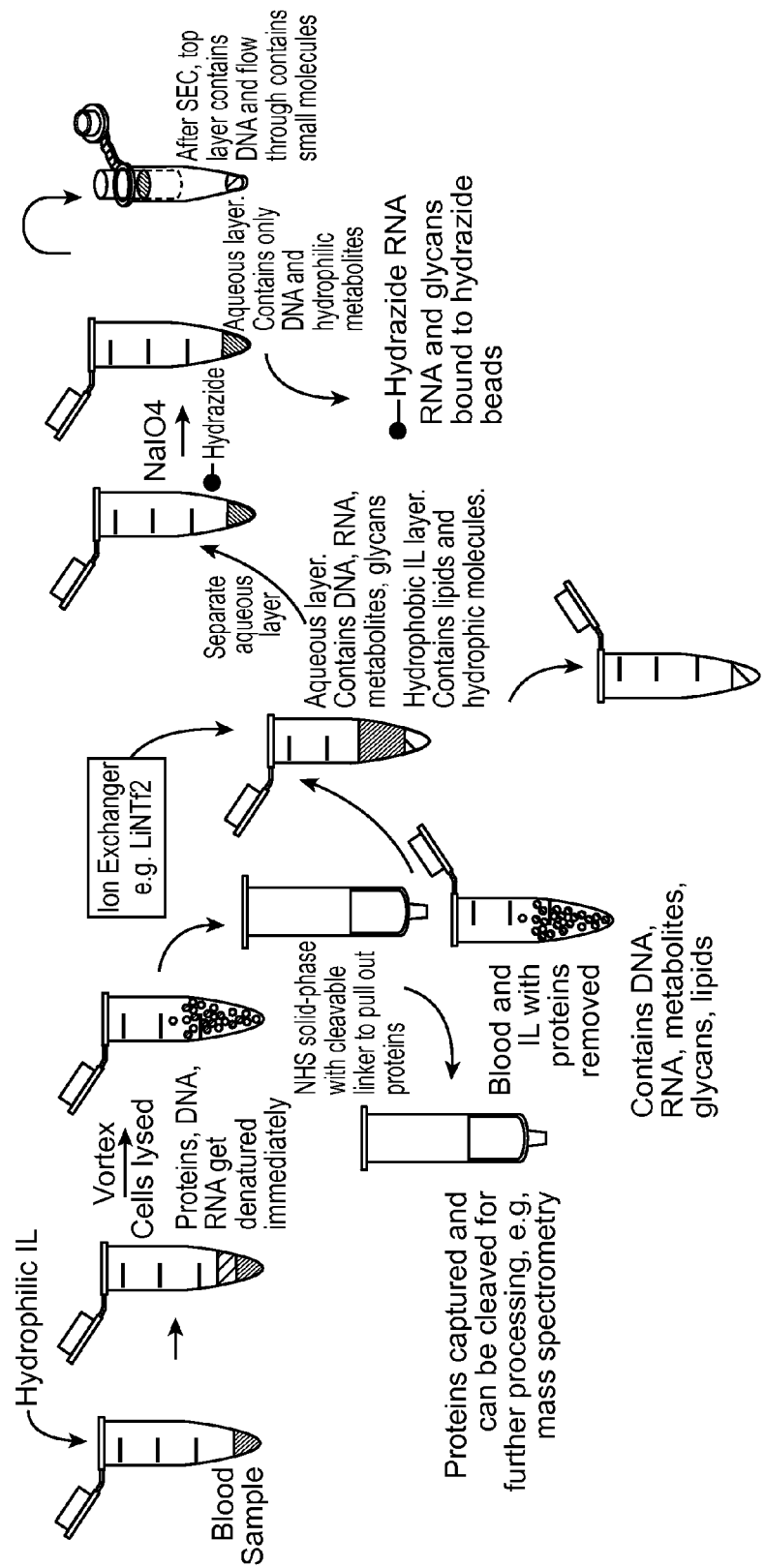
FIG. 4 schematically illustrates workflow for methods according a further embodiment of the subject method.

This embodiment of the method may comprise combining an ionic liquid with a sample and removing the protein from the sample using a solid support comprising an amine-reactive moiety. In certain cases, the protein may be released from the sample and analyzed. This embodiment may further comprise performing ion exchange on the remaining sample, e.g., by adding LiNTf2, and then removing the aqueous layer, which is lipid free. The method may comprise analyzing the lipids. In some cases, the RNA and/or glycans can be reacting them with a solid support, e.g. by oxidation to hydrazide beads. DNA may be purified from the remaining aqueous layer and may be analyzed. In certain cases, the hydrophilic small molecules may be separated from the DNA, e.g., by size exclusion, and optionally analyzed, too. FIG. 4 schematically illustrates one embodiment of this workflow.

Systems for Extracting and Purifying Metabolites from a Biological Sample Having Cells Aspects of the invention further include systems for practicing methods of the invention. In certain embodiments a system for high throughput analysis of cellular metabolites is provided, where the system comprises: a contacting apparatus configured for contacting one or more biological samples with an ionic liquid; a sampling device configured to provide one or more biological samples comprising cells to the contacting apparatus; and an ionic liquid solvent chamber configured to provide one or more ionic liquids to the contacting apparatus.

In certain embodiments, systems may include one or more of (i) a contacting apparatus configured for contacting one or more biological samples with an ionic liquid; (ii) a sampling device configured to provide one or more biological samples comprising cells to the contacting apparatus; (iii) an ionic liquid solvent chamber configured to provide one or more ionic liquids to the contacting apparatus; (iv) a solvent chamber configured to provide one or more organic solvents to the contacting apparatus; (v) an agitator; (vi) an ion exchange composition chamber configured to provide one or more ion exchange compositions to the contacting apparatus; and (vii) a sample analyzer.

In embodiments, systems include a sampling device for delivering one or more biological sample having cells to a contacting apparatus for contacting with one or more ionic liquids. As described above, "biological sample" is used herein to refer to a whole organism, plant, fungi or a subset of animal tissues, cells or component parts which may in certain instances be found in blood, mucus, lymphatic fluid, synovial fluid, cerebrospinal fluid, saliva, amniotic fluid, amniotic cord blood, urine, vaginal fluid and semen. As such, a "biological sample" used herein can refer to a homogenate, lysate or extract prepared from a whole organism or a subset of its tissues, including but not limited to, for example, plasma, serum, spinal fluid, lymph fluid, the external sections of the skin, respiratory, intestinal, and genitourinary tracts, tears, saliva, milk, blood cells, tumors, organs. In embodiments of the invention, a "biological sample" will contain cells from the animal, plants or fungi. A "biological sample" can also refer to a medium, such as a nutrient broth or gel in which an organism has been propagated, which contains cells as well as cellular components, such as proteins or nucleic acid molecules. Biological samples of the invention include cells. The term "cells" is used in its conventional sense to refer to the basic structural unit of living organisms, both eukaryotic and prokaryotic, having at least a nucleus and a cell membrane. In certain embodiments, cells include prokaryotic cells, such as from bacteria. In other embodiments, cells include eukaryotic cells, such as cells obtained from biological samples from animals, plants or fungi.

The contacting apparatus may be any suitable apparatus which allows for a biological sample to be contacted with an ionic liquid. For example, in some embodiments, the contacting apparatus is a sample chamber (e.g., enclosed, sealed, air-tight, open, plate, etc.). In other embodiments, the contacting apparatus is an Eppendorf tube. In other embodiments, the contacting apparatus is a test tube. In yet other embodiments, the contacting apparatus is a glass flask (e.g., beaker, volumetric flask, Erlenmeyer flask, etc.). In still other embodiments, the contacting apparatus is a 96-well plate.

The sampling device configured to provide one or more biological samples having cells to the contacting apparatus may be any convenient device in fluid communication with a source of biological sample having cells, such as for example, a high throughput sample changer having a plurality of sample vials for injection or providing one or more biological samples to the subject systems, a manually injected sample from a syringe, among other sources. As noted above, the biological sample having cells may be processed prior to providing to systems of interest, where the cells have been filtered, sterilized, or otherwise prepared for contacting with the ionic liquid.

Systems of the invention further include an ionic liquid solvent chamber configured to deliver one or more ionic liquids to the contacting apparatus. The ionic liquid solvent chamber may be any suitable solvent reservoir that is capable of storing and/or providing one or more ionic liquids to the contacting apparatus to contact with the biological sample having cells. The ionic liquid solvent chamber may be in fluid communication with one or more source of ionic liquids and may be a single high throughput storage reservoir which can provide ionic liquid as desired for contacting with a plurality of biological samples having cells. Sources of one or more ionic liquids may also be individual vials having a discrete amount of ionic liquid for contacting with a single biological sample. The source of one or more ionic liquids may also be a reservoir with pre-measured aliquots for contacting with a predetermined number of biological samples. For example, source of one or more ionic liquids may include reservoirs which have pre-measured aliquots of ionic liquids for contacting with 2 samples or more, such as 3 samples or more, such as 5 samples or more, such as 10 samples or more, such 25 samples or more, such as 50 samples or more and including pre-measured aliquots of ionic liquid for contacting with 100 biological samples or more. The one or more sources may include a single ionic liquid or may be capable of providing a plurality of different ionic liquids as desired. For example, the source may be capable of storing and providing, as desired, 2 different ionic liquids or more, such as 3 different ionic liquids or more, such as 5 different ionic liquids or more, and including 10 different ionic liquids or more. Depending on the particular design of the ionic liquid solvent chamber, the chamber may further include one or more inlets for delivering the ionic solvent to the contacting apparatus to contact with one or more biological samples having cells. In certain embodiments, systems of the invention include one or more inlets for injecting ionic liquid into a vial containing the biological sample.

As described above, ionic liquids of the invention destabilize, disrupt or denature enzyme structure. Any convenient ionic liquid may be provided to systems of in the invention so long as the ionic liquid destabilizes, disrupts and/or denatures enzyme structure. In certain embodiments, the ionic liquid solvent chamber is configured to deliver one or more hydrophilic ionic liquids to the contacting apparatus. In other embodiments, the ionic liquid solvent chamber provides one or more hydrophobic ionic liquids to the contacting apparatus.

In certain embodiments, the ionic liquid solvent chamber is configured to provide to the contacting apparatus ionic liquid which includes a cation selected from the group consisting of:

a)

Formula (I)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or b)

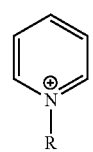

Formula (II)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or c)

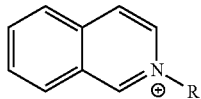

Formula (III)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or d)

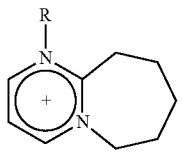

Formula (IV)

where R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or e)

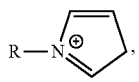

Formula (V)

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or f)

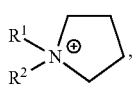

Formula (VI)

where each of $R^1$ and $R^2$ is independently hydrogen, alkyl, substituted alkyl, aryl, substituted aryl, arylalkyl, heteroalkyl, substituted heteroalkyl, heteroaryl, substituted heteroaryl, heteroarylalkyl, substituted heteroarylalkyl.

In certain embodiments, the ionic liquid includes a cation having Formula (I):

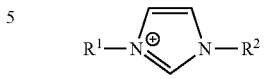

where each of $R^1$ and $R^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl. In some instances, $R^1$ is methyl and $R^2$ is butyl. In certain embodiments, ionic liquids of interest include 1-butyl-3-methyl-imidazol-3-ium.

In some embodiments, the ionic liquid includes a cation selected from the group consisting of sulfonium cations, phosphonium cations, tetraalkyl ammonium cations and pyrazolium cations. In other embodiments, the ionic liquid is a compound selected from the group consisting of 1,2,4-trimethylpyrazolium methylsulfate, methyl-trioctylammonium bis(trifluoromethylsulfonyl)imide, trihexyltetradecylphosphonium bromide and 5-(trifluoromethyl) dibenzothiophenium trifluoromethanesulfonate.

Systems of the invention may further include a solvent chamber configured to provide one or more organic solvents to the contacting apparatus. The organic solvent chamber may be any convenient reservoir that is capable of storing and/or providing one or more organic solvents and may be a single high throughput storage reservoir which can provide organic solvent as desired for contacting with a ionic liquid cellular sample or may be individual vials which can contain a discrete amount of organic solvent for contacting with a ionic liquid cellular sample. The source of one or more organic solvents may in certain embodiments be a reservoir with pre-measured aliquots for contacting with a predetermined number of ionic liquid cellular samples. For example, the source may include reservoirs which have pre-measured aliquots of organic solvent for contacting with 2 samples or more, such as 3 samples or more, such as 5 samples or more, such as 10 samples or more, such 25 samples or more, such as 50 samples or more and including pre-measured aliquots of organic solvent for contacting with 100 samples or more. The one or more sources may include a single organic solvent or may be capable of providing a plurality of different organic solvents, as desired. For example, the source may be capable of storing and providing, as desired, 2 different organic solvents or more, such as 3 different organic solvents or more, such as 5 different organic solvents or more, and including 10 different organic solvents or more. Depending on the particular design of the organic solvent chamber, the chamber may further include one or more inlets for contacting the organic solvent with the ionic liquid cellular sample. In certain embodiments, systems of the invention include one or more inlets for injecting organic solvent into the vial containing the ionic liquid cellular sample.

In some embodiments, the organic solvent is a hydrophobic or non-polar organic solvent. Hydrophobic or non-polar organic solvents of interest include, but are not limited to pentane, hexane, heptane, octane, diethyl ether, and chloroform.

As discussed above, microdroplet dispersions may be formed from the ionic liquid cellular sample-organic solvent two phase composition by agitation. As such, systems of the invention may further include an agitator for mixing the ionic liquid cellular sample-organic solvent two phase composition to form a microdroplet dispersion composition. The agitator may be any convenient agitator sufficient for mixing the subject compositions and forming a turbid microdroplet dispersion composition. Agitators or interest include, but are not limited to vortexers, sonicators, shakers (e.g., manual, mechanical, or electrically powered shakers), rockers, oscillating plates, magnetic stirrers, static mixers, rotators, blenders, mixers, tumblers, orbital shakers, among other agitating protocols.

Systems of the invention may further include an ion exchange composition chamber configured to provide one or more ion exchange compositions to the contacting apparatus. The ion exchange composition chamber may be any convenient reservoir that is capable of storing and/or providing one or more ion exchange compositions and may be a single high throughput storage reservoir which can provide the ion exchange composition as desired for contacting with microdroplet dispersion composition or may be individual vials having a discrete amount of ion exchange composition. The ion exchange composition chamber may alternative include a source of one or more ion exchange compositions in pre-measured aliquots. For example, source of one or more ion exchange composition may include reservoirs which have pre-measured aliquots for contacting with 2 microdroplet dispersion compositions or more, such as 3 microdroplet dispersion compositions or more, such as 5 microdroplet dispersion compositions or more, such as 10 microdroplet dispersion compositions or more, such 25 microdroplet dispersion compositions or more, such as 50 microdroplet dispersion compositions or more and including pre-measured aliquots of ion exchange compositions for contacting with 100 microdroplet dispersion compositions or more. The one or more sources may include a single ion exchange composition or may be capable of providing a plurality of different ion exchange compositions, as desired. For example, the source may be capable of storing and providing, as desired, 2 different ion exchange compositions or more, such as 3 different ion exchange compositions or more, such as 5 different ion exchange compostions or more, and including 10 different ion exchange compositions or more. Depending on the particular design of the ion exchange composition chamber, the chamber may further include one or more inlets for contacting the ion exchange composition with the microdroplet dispersion composition. In certain embodiments, systems of the invention include one or more inlets for injecting the ion exchange composition into the vial containing the microdroplet dispersion composition.

In certain embodiments, the source of one or more ion exchange compositions includes a salt having an anion selected from the group consisting of boron tetrafluoride, bis-(2,4,4-trimethylpentyl)phosphinate, bis-(trifluoromethyl)imide, bis[(trifluoromethane)sulfonyl]imide, bis-(trifluoromethylsulfonyl)methane, bis-biphenyldiolatoborate, bis-malonatoborate, bis-oxalatoborate, bis-(pentafluoroethyl)phosphinate, bis-salicylatoborate, bromine, butylsulfate, chloride, perchlorate, decanoate, dicyanamide, ethylsulfate, iodide, methylsulfate, octylsulfate, hexafluorophosphate, tetracyanoborate, toluene-4-sulfonate, trifluoromethane-sulfonate, tris-(nonafluorobutyl)-trifluorophosphate and tris-(pentafluoroethyl)trifluorophosphate. In certain instances, the ion exchange composition includes lithium bis[(trifluoromethane)sulfonyl]imide ($LiNTf_2$) and the anion exchange with the ionic liquid of the dispersed microdroplets includes the formation of a new ionic salt having a bis[(trifluoromethane)sulfonyl]imide ($NTf_2$) anion.

Systems of the invention may also include a sample analyzer. In certain embodiments, the sample analyzer may be liquid chromatography-mass spectrometry or gas chromatography-mass spectrometry systems. For example, the apparatus may include analytical separation device such as a liquid chromatograph (LC), including a high performance liquid chromatograph (HPLC), a micro- or nano-liquid chromatograph or an ultra high pressure liquid chromatograph (UHPLC) device, a capillary electrophoresis (CE), or a capillary electrophoresis chromatograph (CEC) apparatus. However, any manual or automated injection or dispensing pump system may be used. For instance, a the subject sample may be applied to the LC-MS system by employing a nano- or micropump in certain embodiments.

Mass spectrometer systems may be any convenient mass spectrometry system, which in general contains an ion source for ionizing a sample, a mass analyzer for separating ions, and a detector that detects the ions. In certain cases, the mass spectrometer may be a so-called "tandem" mass spectrometer that is capable of isolating precursor ions, fragmenting the precursor ions, and analyzing the fragmented precursor ions. Such systems are well known in the art (see, e.g., U.S. Pat. Nos. 7,534,996, 7,531,793, 7,507,953, 7,145,133, 7,229,834 and 6,924,478) and may be implemented in a variety of configurations. In certain embodiments, tandem mass spectrometry may be done using individual mass analyzers that are separated in space or, in certain cases, using a single mass spectrometer in which the different selection steps are separated in time. Tandem MS "in space" involves the physical separation of the instrument components (QqQ or QTOF) whereas a tandem MS "in time" involves the use of an ion trap.

An example mass spectrometer system may contain an ion source containing an ionization device, a mass analyzer and a detector. As is conventional in the art, the ion source and the mass analyzer are separated by one or more intermediate vacuum chambers into which ions are transferred from the ion source via, e.g., a transfer capillary or the like. Also as is conventional in the art, the intermediate vacuum chamber may also contain a skimmer to enrich analyte ions (relative to solvent ions and gas) contained in the ion beam exiting the transfer capillary prior to its entry into the ion transfer optics (e.g., an ion guide, or the like) leading to a mass analyzer in high vacuum.

The ion source may rely on any type of ionization method, including but not limited to electrospray ionization (ESI), atmospheric pressure chemical ionization (APCI), electron impact (EI), atmospheric pressure photoionization (APPI), matrix-assisted laser desorption ionization (MALDI) or inductively coupled plasma (ICP) ionization, for example, or any combination thereof (to provide a so-called "multimode" ionization source). In one embodiment, the precursor ions may be made by EI, ESI or MALDI, and a selected precursor ion may be fragmented by collision or using photons to produce product ions that are subsequently analyzed.

Likewise, any of a variety of different mass analyzers may be employed, including time of flight (TOF), Fourier transform ion cyclotron resonance (FTICR), ion trap, quadrupole or double focusing magnetic electric sector mass analyzers, or any hybrid thereof. In one embodiment, the mass analyzer may be a sector, transmission quadrupole, or time-of-flight mass analyzer.

Aspects of the invention may further include high-throughput and computer controlled systems for practicing methods of the invention, where the systems further include one or more computers for automation or semi-automation of a system for practicing methods of the invention. In certain embodiments, systems include a computer having a computer readable storage medium with a computer program stored thereon, where the computer program when loaded on the computer includes algorithm for contacting one or more biological sample with an amount of ionic liquid sufficient to lyse cells and denature intracellular metabolic enzymes in the biological sample; algorithm for mixing the ionic liquid with an organic solvent to produce a first ionic liquid-organic solvent two-phase composition; algorithm for employing an agitator to agitate the first ionic liquid-organic solvent two-phase composition to produce a dispersed microdroplet composition; algorithm for contacting dispersed microdroplet composition with an ion exchange composition to produce a second ionic liquid-organic solvent two-phase composition; algorithm for separating the ionic liquid from the organic solvent and extracting metabolites from the ionic liquid; and instructions for identifying one or more metabolites extracted from the ionic liquid.

In embodiments of the invention, the system includes an input module, a processing module and an output module. In some embodiments, the subject systems may include an input module such that parameters or information about each of the ionic liquids, organic solvents, ion exchange compositions, biological samples having cells, etc. may be inputted into the computer. The processing module includes memory having a plurality of instructions for performing the steps of the subject methods, i.e., contacting one or more biological sample with an amount of ionic liquid sufficient to lyse cells and denature intracellular metabolic enzymes in the biological sample; mixing the ionic liquid with an organic solvent to produce a first ionic liquid-organic solvent two-phase composition; employing an agitator to agitate the first ionic liquid-organic solvent two-phase composition to produce a dispersed microdroplet composition; contacting dispersed microdroplet composition with an ion exchange composition to produce a second ionic liquid-organic solvent two-phase composition; separating the ionic liquid from the organic solvent and extracting metabolites from the ionic liquid; and identifying one or more of the metabolites extracted from the ionic liquid.

After the processing module has performed one or more of the steps of the subject methods, an output module communicates the results (e.g., characterization of the one or more metabolites) to the user, such as by displaying on a monitor or by printing a report.

The subject systems may include both hardware and software components, where the hardware components may take the form of one or more platforms, e.g., in the form of servers, such that the functional elements, i.e., those elements of the system that carry out specific tasks (such as managing input and output of information, processing information, etc.) of the system may be carried out by the execution of software applications on and across the one or more computer platforms represented of the system.

Systems may include a display and operator input device. Operator input devices may, for example, be a keyboard, mouse, or the like. The processing module includes a processor which has access to a memory having instructions stored thereon for performing one or more of the steps of the subject methods, i.e., contacting one or more biological sample with an amount of ionic liquid sufficient to lyse cells and denature intracellular metabolic enzymes in the biological sample; mixing the ionic liquid with an organic solvent to produce a first ionic liquid-organic solvent two-phase composition; employing an agitator to agitate the first ionic liquid-organic solvent two-phase composition to produce a dispersed microdroplet composition; contacting dispersed microdroplet composition with an ion exchange composition to produce a second ionic liquid-organic solvent two-phase composition; separating the ionic liquid from the organic solvent and extracting metabolites from the ionic liquid; and identifying one or more of the metabolites extracted from the ionic liquid. The processing module may include an operating system, a graphical user interface (GUI) controller, a system memory, memory storage devices, and input-output controllers, cache memory, a data backup unit, and many other devices. The processor may be a commercially available processor or it may be one of other processors that are or will become available. The processor executes the operating system and the operating system interfaces with firmware and hardware in a well-known manner, and facilitates the processor in coordinating and executing the functions of various computer programs that may be written in a variety of programming languages, such as Java, Perl, C++, other high level or low level languages, as well as combinations thereof, as is known in the art. The operating system, typically in cooperation with the processor, coordinates and executes functions of the other components of the computer. The operating system also provides scheduling, input-output control, file and data management, memory management, and communication control and related services, all in accordance with known techniques.

The system memory may be any of a variety of known or future memory storage devices. Examples include any commonly available random access memory (RAM), magnetic medium such as a resident hard disk or tape, an optical medium such as a read and write compact disc, flash memory devices, or other memory storage device. The memory storage device may be any of a variety of known or future devices, including a compact disk drive, a tape drive, a removable hard disk drive, or a diskette drive. Such types of memory storage devices typically read from, and/or write to, a program storage medium (not shown) such as, respectively, a compact disk, magnetic tape, removable hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage device used in conjunction with the memory storage device.

In some embodiments, a computer program product is described comprising a computer usable medium having control logic (computer software program, including program code) stored therein. The control logic, when executed by the processor the computer, causes the processor to perform functions described herein. In other embodiments, some functions are implemented primarily in hardware using, for example, a hardware state machine. Implementation of the hardware state machine so as to perform the functions described herein will be apparent to those skilled in the relevant arts.

Memory may be any suitable device in which the processor can store and retrieve data, such as magnetic, optical, or solid state storage devices (including magnetic or optical disks or tape or RAM, or any other suitable device, either fixed or portable). The processor may include a general purpose digital microprocessor suitably programmed from a computer readable medium carrying necessary program code. Programming can be provided remotely to processor through a communication channel, or previously saved in a computer program product such as memory or some other portable or fixed computer readable storage medium using any of those devices in connection with memory. For example, a magnetic or optical disk may carry the programming, and can be read by a disk writer/reader. Systems of the invention also include programming, e.g., in the form of computer program products, algorithms for use in practicing the methods as described above. Programming according to the present invention can be recorded on computer readable media, e.g., any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media.

The processor may also have access to a communication channel to communicate with a user at a remote location By remote location is meant the user is not directly in contact with the system and relays input information to an input manager from an external device, such as a computer connected to a Wide Area Network ("WAN"), telephone network, satellite network, or any other suitable communication channel, including a mobile telephone (i.e, smartphone). In these embodiments, input manager receives information, e.g., coagulation activity data, chemical makeup data, molecular structure data, etc., from a user e.g., over the Internet, telephone or satellite network. Input manager processes and forwards this information to the processing module. These functions are performed using any convenient technique.

Output controllers may include controllers for any of a variety of known display devices for presenting information to a user, whether a human or a machine, whether local or remote. If one of the display devices provides visual information, this information typically may be logically and/or physically organized as an array of picture elements. A graphical user interface (GUI) controller may include any of a variety of known or future software programs for providing graphical input and output interfaces between the system and a user, and for processing user inputs. The functional elements of the computer may communicate with each other via system bus. Some of these communications may be accomplished in alternative embodiments using network or other types of remote communications. The output manager may also provide information generated by the processing module to a user at a remote location, e.g, over the Internet, phone or satellite network, in accordance with known techniques. The presentation of data by the output manager may be implemented in accordance with a variety of known techniques. As some examples, data may include SQL, HTML or XML documents, email or other files, or data in other forms. The data may include Internet URL addresses so that a user may retrieve additional SQL, HTML, XML, or other documents or data from remote sources. The one or more platforms present in the subject systems may be any type of known computer platform or a type to be developed in the future, although they typically will be of a class of computer commonly referred to as servers. However, they may also be a main-frame computer, a work station, or other computer type. They may be connected via any known or future type of cabling or other communication system including wireless systems, either networked or otherwise. They may be co-located or they may be physically separated. Various operating systems may be employed on any of the computer platforms, possibly depending on the type and/or make of computer platform chosen. Appropriate operating systems include Windows NT®, Windows XP, Windows 7, Sun Solaris, Linux, OS/400, Compaq Tru64 Unix, SGI IRIX, Siemens Reliant Unix, and others.

Kits

Also provided by this disclosure are kits for practicing the subject method as described above. A subject kit may contain one or more of: (i) one or more ionic liquids; (ii) one or more organic solvents; and (iii) an ion exchange composition. The kit may also include containers, measurement devices and instruments for performing the subject methods, e.g., vials, agitators, shakers, vortexers, pipets, filter membranes, etc. The various components of the kit may be present in separate containers or certain compatible components may be pre-combined into a single container, as desired.

In addition to above-mentioned components, the subject kits may further include instructions for using the components of the kit to practice the subject methods, i.e., to provide instructions for sample analysis. The instructions for practicing the subject methods are generally recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or subpackaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g., via the internet, are provided. An example of this embodiment is a kit that includes a web address where the instructions can be viewed and/or from which the instructions can be downloaded. As with the instructions, this means for obtaining the instructions is recorded on a suitable substrate.

Utility

The method described above may be used to analyze metabolites in any of a variety of different cells, including bacterial cells such as *E. coli* cells, and eukaryotic cells such as cells of a lower eukaryote, e.g., yeast, or a higher eukaryote such as a plant (e.g., monocot or dicot) or an animal (e.g., an insect, amphibian, or mammalian etc.). In certain cases, the source of the cells may or may not have a cell wall, and in certain embodiments, the cells may be photosynthetic or non-photosynthetic, oleaginous or non-oleaginous. In particular embodiments, the cells are not algae. The cells may be cultured cells, or, in certain embodiments, cells from a tissue.

The method described above may be used for metabolomics studies, i.e., systematic studies of the unique chemical fingerprints that are associated with specific cellular processes and the study of their metabolite profiles. The metabolome represents the complete set of small-molecule metabolites (such as metabolic intermediates, hormones and other signaling molecules, and secondary metabolites) to be found within a biological sample, such as a single organism The subject method may be employed in a variety of drug discovery, research and diagnostic applications. For example, a subject method may be employed in a variety of applications that include, but are not limited to, diagnosis or monitoring of a disease or condition (where the presence of metabolic profile is indicative of a disease or condition), discovery of drug targets (where, e.g., of metabolic profile associated with a disease or condition and may be targeted for drug therapy), drug screening (where the effects of a drug are monitored by assessing a metabolic profile), determining drug susceptibility (where drug susceptibility is associated with a particular metabolic profile) and basic research (where is it desirable to identify the a metabolic profile in a sample, or, in certain embodiments, the relative levels of a particular metabolites in two or more samples).

In certain embodiments, relative levels of a set of metabolites in two or more different nucleic acid samples may be obtained using the above methods, and compared. In these embodiments, the results obtained from the above-described methods are usually normalized to the total amount of a control metabolite, and compared. This may be done by comparing ratios, or by any other means. In particular embodiments, the nucleic acid profiles of two or more different samples may be compared to identify metabolites that are associated with a particular disease or condition.

In some examples, the different samples may consist of an "experimental" sample, i.e., a sample of interest, and a "control" sample to which the experimental sample may be compared. In many embodiments, the different samples are pairs of cell types, one cell type being a cell type of interest, e.g., an abnormal cell, and the other a control, e.g., normal, cell. If two fractions of cells are compared, the fractions are usually the same fraction from each of the two cells. In certain embodiments, however, two fractions of the same cell may be compared. Exemplary cell type pairs include, for example, cells that are treated (e.g., with environmental or chemical agents such as peptides, hormones, altered temperature, growth condition, physical stress, cellular transformation, etc.), and a normal cell (e.g., a cell that is otherwise identical to the experimental cell except that it is not immortal, infected, or treated, etc.); cells isolated from a tissue biopsy (e.g., from a tissue having a disease such as colon, breast, prostate, lung, skin cancer, or infected with a pathogen etc.) and normal cells from the same tissue, usually from the same patient; cells grown in tissue culture that are immortal (e.g., cells with a proliferative mutation or an immortalizing transgene), infected with a pathogen or a cell isolated from a mammal with a cancer, a disease, a geriatric mammal, or a mammal exposed to a condition, and a cell from a mammal of the same species, preferably from the same family, that is healthy or young; and differentiated cells and non-differentiated cells from the same mammal (e.g., one cell being the progenitor of the other in a mammal, for example).

EXAMPLES

The following example is offered for illustrative purposes only, and is not intended to limit the scope of the present invention in any way.
Objectives:
Sample processing and preparation for metabolomic analysis which incorporates into its steps one or more of the following:
1. Quenching—Stopping any metabolic processes such that an accurate snapshot of the current metabolic state of the cells under study can be evaluated.
2. Cell Lysis—In certain embodiments, the intercellular metabolome is measured. This requires that the cell be lysed and the contents be separated from the extracellular medium.
3. Metabolite Extraction: Metabolic components are extracted from all other cellular components (proteins, nucleic acids, lipids).
4. Metabolite Concentration: Depending on the sensitivity of the analytical technique and the requirements of the experiment, in certain embodiments, the extracted metabolites are concentrated prior to analysis.

Brief Description of Example Techniques According to Certain Embodiments:

(a) Dispersive Liquid Liquid Microextraction (DLLME), is a sample preparation technique based on formation of a turbid solution by quickly injecting a mixture of an extraction solvent and a disperser solvent into an aqueous solution. The extraction solvent is hydrophobic and of higher density than water while the disperser is miscible with both aqueous and organic phases. The obtained turbid solution results in the large contact area between the fine extraction solvent droplets and aqueous analyte solution, remarkably decreasing the extraction time and increasing the extraction efficiency. DLLME has been widely applied to arrange of analytical samples, primarily environmental.

(b) Ionic Liquids combined with DLLME for preparing a sample where the compounds of interest are extracted into the ionic liquid.

In example embodiments, a method for metabolic sample preparation based on Dispersive Liquid Liquid Microextraction (DLLME) utilizing Ionic Liquids (IL) in which the novel ionic liquids rapidly and effectively denature metabolic enzymes to quench metabolism and simultaneously extracting hydrophilic metabolites in the background of cellular components.

The subject methods include the use of Ionic Liquids in combination with DLLME to simultaneously lyse cells and denature metabolic enzymes in such a way as to rapidly quench metabolism. In practicing the subject methods, the workflow will have at least the following benefits:

1. Rapid Cell Lysis and Metabolic Quenching without the use of cryo-conditions.
2. Rapid separation of extra- and intra-cellular components
3. Rapid and Efficient fractionation of intracellular components into hydrophilic and hydrophobic fractions.
4. Robust technique applied to a range of cellular systems without the need of optimization for each cell type
5. Easily adapted to automated, robotic platforms and multiwell plate sample formats.

Example 1

With reference to FIG. 1, an example workflow may include:
Step 1: Cell Suspension is transferred to a filter tube and rapidly filtered to separate culture media and extra-cellular components from the cell mass.
Step 2: The filtered cells are resuspended in the hydrophilic Ionic Liquid. This would simultaneously rapidly lyse the cells and denature the metabolic enzymes and consequently quench metabolic processes.
Step 3: The Ionic Liquid containing the sample is mixed with a hydrophobic organic liquid.
Step 4: The two phase system is agitated forming a dispersed system of ionic liquid microdroplets with a high surface area (without the addition of a dispersant). Hydrophobic components (such as lipids) are extracted into the organic phase. Proteins precipitate. The hydrophilic metabolite analytes are extracted into the ionic liquid.
Step 5: An Ion Exchanger (e.g., $LiNTf_2$) is added causing the Ionic Liquid microdroplets to condense in metathesis reaction and separate from the organic layer.
Step 6: The Ionic liquid is removed from the metabolite analytes by solid phase microextraction under conditions where the ionic liquid itself does not act as an elutropic solvent during the loading of analytes onto stationary phase.

In the above example, ionic liquids of interest have the following to have the following characteristics:
Denature Proteins/Quench Metabolites
Lyse Cells (Yeast)
Extract/Solublize Metabolites of interest
Precipitate/Remove Proteins
Immiscible w/Organic for 2 phase extraction DLLME
Metabolites can be separated by liquid chromatography (e.g., HPLC)
In one example, the ionic liquid may include:

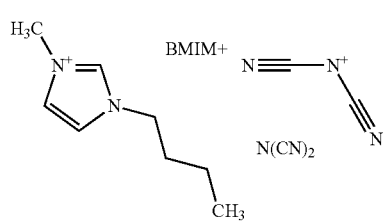

Alternative, room temperature ionic liquids may include a scaffold structure such as a 1, 3 substituted imidazolium cation, a salt can be structured, by varying the R groups and the counter ion to optimize a range of physicochemical properties.

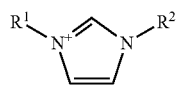

1, 3 substituted imidazol-3-ium

For example, in the structure show above, $R^1$ and $R^2$ were adapted based on general physico-chemical properties such as density, solubility, vapor pressure, as desired. In addition, specific substitutions can be made on the R-groups to enhance specific chemical interactions with target groups.

Example 2

Figure 2:
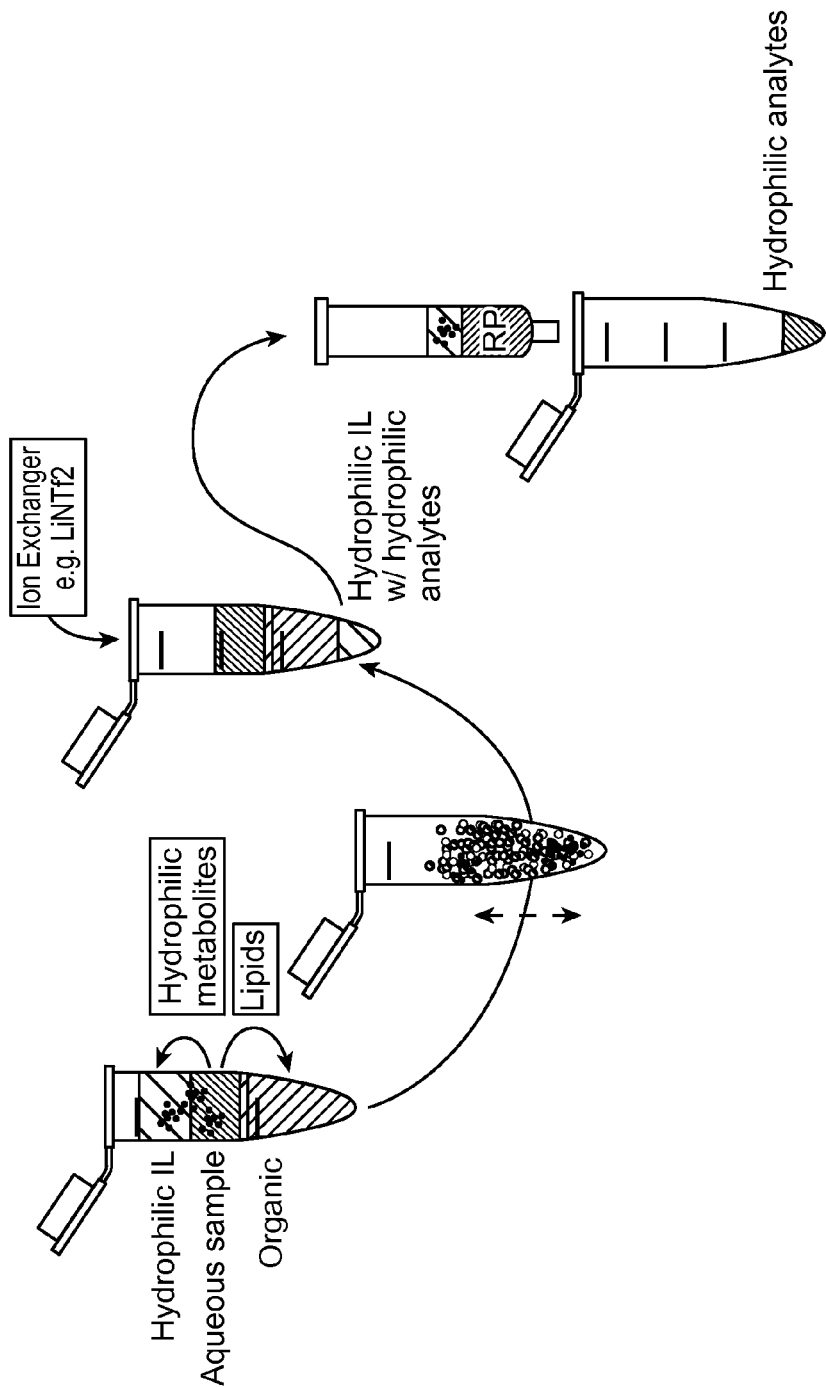
FIG. 2 schematically illustrates workflow for methods according another embodiment of the subject method.

As shown in FIG. 2, an example workflow similar to the steps described above in Example 1, may include a three phase system in which an ionic liquid is used that can interact with metabolites to extract them from aqueous solution intermediate between the organic solution.

Step 1: Cell Suspension is transferred to a filter tube and rapidly filtered to separate culture media and extra-cellular components from the cell mass.

Step 2: The filtered cells are resuspended as an aqueous solution in a hydrophilic Ionic Liquid. This would simultaneously rapidly lyse the cells and denature the metabolic enzymes and consequently quench metabolic processes.

Step 3: The Ionic Liquid containing the sample is mixed with a hydrophobic organic liquid.

Step 4: The three phase system is agitated forming a dispersed system of ionic liquid microdroplets with a high surface area (without the addition of a dispersant). Hydrophobic components (such as lipids) are extracted into the organic phase. Proteins precipitate. The hydrophilic metabolite analytes are extracted into the ionic liquid.

Step 5: An Ion Exchanger (e.g., $LiNTf_2$) is added causing the Ionic Liquid microdroplets to condense in metathesis reaction and separate from the organic and aqueous layers.

Step 6: The Ionic liquid is removed from the metabolite analytes by solid phase microextraction under conditions where the ionic liquid itself does not act as an elutropic solvent during the loading of analytes onto stationary phase.

Example 3

Figure 3:
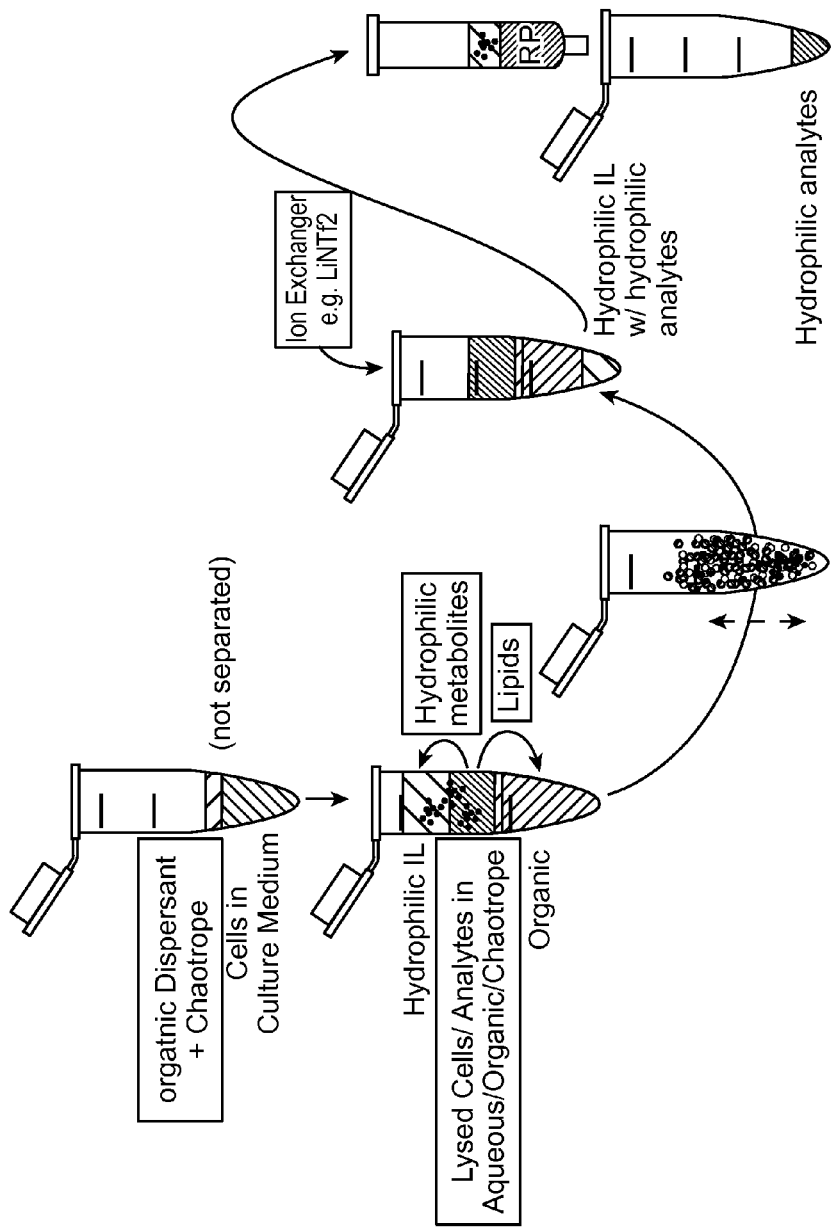
FIG. 3 schematically illustrates workflow for methods according a further embodiment of the subject method.

As shown in FIG. 3, an example workflow similar to the steps described above in Example 2, may include a three phase system in which an ionic liquid is used that can interact with metabolites to extract them from aqueous solution intermediate between the organic solution with the addition of a chaotrope and dispersant to enhance microdroplet formation.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the embodiments shown and described herein. Rather, the scope and spirit of present invention is embodied by the appended claims.

The invention claimed is:

1. A method comprising:
lysing cells of a biological sample;
contacting the biological sample with an amount of ionic liquid sufficient to denature intracellular metabolic enzymes in the biological sample to produce a contacted cellular sample;
mixing the contacted cellular sample with an organic solvent to produce a dispersed microdroplet ionic liquid-organic solvent composition; and
contacting the dispersed microdroplet ionic liquid-organic solvent composition with an ion exchange composition to produce a second ionic liquid-organic solvent composition.

2. The method according to claim 1, wherein contacting the biological sample with the ionic liquid lyses the cells of the biological sample.

3. The method according to claim 1, wherein the dispersed microdroplet ionic liquid-organic solvent composition is a two-phase composition.

4. The method according to claim 1, wherein the biological sample is an aqueous solution and the dispersed microdroplet ionic liquid-organic solvent composition is a three-phase composition.

5. The method according to claim 1, wherein the ion exchange composition is a second ionic liquid.

6. The method according to claim 1, wherein the ion exchange composition comprises lithium bis[(trifluoromethane)sulfonyl] imide (LiNTf$_2$).

7. The method according to claim 1, further comprising extracting metabolites of the cells from the ionic liquid.

8. The method according to claim 1, wherein the ionic liquid comprises a cation selected from the group consisting of:

a)

Formula (I)

wherein each of R$^1$ and R$^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or b)

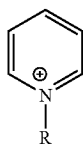

Formula (II)

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or c)

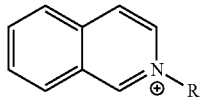

Formula (III)

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or d)

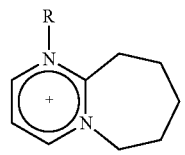

Formula (IV)

wherein R is hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or e)

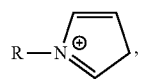

Formula (V)

wherein each of R$^1$ and R$^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl; or f)

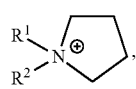

Formula (VI)

wherein each of R$^1$ and R$^2$ is independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl, substituted heteroarylalkyl.

9. The method according to claim 1, wherein the ionic liquid comprises 1-butyl-3-methyl-imidazol-3-ium.

10. The method according to claim 1, wherein the biological sample is contacted with the ionic liquid at room temperature.

11. The method according to claim 1, wherein the method further comprises filtering the biological sample to remove culture media and extracellular components from the cells prior to contacting with the ionic liquid.

12. The method of claim 1, wherein the cells do not have cell wall.

* * * * *

UNITED STATES PATENT AND TRADEMARK OFFICE
CERTIFICATE OF CORRECTION

Page 1 of 2

PATENT NO. : 10,012,574 B2
APPLICATION NO. : 14/205100
DATED : July 3, 2018
INVENTOR(S) : James Alexander Apffel, Jr.

It is certified that error appears in the above-identified patent and that said Letters Patent is hereby corrected as shown below:

In the Drawings

On sheet 3 of 4, in Figure 3, Line 1, delete "orgatnic" and insert -- organic --, therefor.

In the Specification

In Column 5, Line 43, delete "hexylene," and insert -- hexalene, --, therefor.

In Column 6, Line 9, delete "phenyl-napthyl," and insert -- phenyl-naphthyl, --, therefor.

In Column 6, Line 10, delete "napthyl," and insert -- naphthyl, --, therefor.

In Column 6, Line 15, delete "phenylnapthyl," and insert -- phenylnaphthyl, --, therefor.

In Column 6, Line 52, delete ".=N—N=," and insert -- =N—N=, --, therefor.

In Column 7, Line 23, delete "heterorylalkynyl" and insert -- heteroarylalkynyl --, therefor.

In Column 7, Lines 42-43, delete "hexylene," and insert -- hexalene, --, therefor.

In Column 10, Line 18, delete "acetylaldehyde," and insert -- acetaldehyde, --, therefor.

In Column 11, Line 45, after "293K)" insert -- . --.

In Column 11, Line 59, delete "phophoglycerate" and insert -- phosphoglycerate --, therefor.

In Column 11, Line 64, delete "bisphophate" and insert -- bisphosphate --, therefor.

In Column 14, Line 56, delete "extraced" and insert -- extracted --, therefor.

Signed and Sealed this
Eighteenth Day of September, 2018

Andrei Iancu
*Director of the United States Patent and Trademark Office*

CERTIFICATE OF CORRECTION (continued)
U.S. Pat. No. 10,012,574 B2

In Column 17, Line 14, delete "a the" and insert -- the --, therefor.

In Column 23, Line 40, delete "compostions" and insert -- compositions --, therefor.

In Column 24, Line 12, delete "a the" and insert -- the --, therefor.

In Column 27, Line 18, delete "location" and insert -- location. --, therefor.

In Column 28, Line 57, after "organism" insert -- . --.

In Column 29, Line 3, after "identify" delete "the".

In Column 30, Line 35, after "components" insert -- . --.

In Column 30, Line 39, after "type" insert -- . --.

In Column 30, Line 66, delete "elutropic" and insert -- eluotropic --, therefor.

In Column 31, Line 5, delete "Solublize" and insert -- Solubilize --, therefor.

In Column 32, Line 1, delete "elutropic" and insert -- eluotropic --, therefor.